(12) United States Patent
Myung et al.

(10) Patent No.: US 11,898,171 B2
(45) Date of Patent: Feb. 13, 2024

(54) COMPOSITION AND METHOD FOR INCREASING PRODUCTION OF BACTERIOPHAGE USING REACTIVE OXYGEN SPECIES

(71) Applicant: LyseNTech, Yongin-si (KR)

(72) Inventors: Heejoon Myung, Yongin-si (KR); Yunyeol Jo, Yongin-si (KR)

(73) Assignee: LYSENTECH, Yongin-si (KR)

( * ) Notice: Subject to any disclaimer, the term of this patent is extended or adjusted under 35 U.S.C. 154(b) by 1023 days.

(21) Appl. No.: 16/642,599

(22) PCT Filed: Aug. 22, 2018

(86) PCT No.: PCT/KR2018/009663
§ 371 (c)(1),
(2) Date: Feb. 27, 2020

(87) PCT Pub. No.: WO2019/045356
PCT Pub. Date: Mar. 7, 2019

(65) Prior Publication Data
US 2020/0347362 A1    Nov. 5, 2020

(30) Foreign Application Priority Data
Aug. 28, 2017  (KR) .......................... 10-2017-0108588

(51) Int. Cl.
*C12N 7/00*       (2006.01)

(52) U.S. Cl.
CPC ...... *C12N 7/00* (2013.01); *C12N 2795/00051* (2013.01); *C12N 2795/10151* (2013.01)

(58) Field of Classification Search
CPC ........................ C12N 7/00; C12N 2795/00051
See application file for complete search history.

(56) References Cited

U.S. PATENT DOCUMENTS 7,622,293 B2    11/2009    Sulakvelidze et al.

FOREIGN PATENT DOCUMENTS

KR    10-0941892 B1    2/2010

OTHER PUBLICATIONS

Slade et al. Effect of oxygen and peroxide on Bacteroides fragilis cell and phage survival after treatment with DNA damaging agents. FEMS Microbiology Letters 24 (1984) 159-163. (Year: 1984).*
Slade et al. Peroxide inducible phage reactivation in Bacteroides fragilis. FEMS Microbiology Letters 20 (1983) 401-405. (Year: 1983).*
Kim MS, Myung H. Complete genome of *Staphylococcus aureus* phage SA11. J Virol. Sep. 2012;86(18):10232. (Year: 2012).*
Furusawa T, Iwano H, Higuchi H, Yokota H, Usui M, Iwasaki T, Tamura Y. Bacteriophage can lyse antibiotic-resistant Pseudomonas aeruginosa isolated from canine diseases. J Vet Med Sci. Jul. 1, 2016;78(6):1035-8. (Year: 2016).*
Loś JM, Loś M, Wegrzyn A, Wegrzyn G. Hydrogen peroxide-mediated induction of the Shiga toxin-converting lambdoid prophage ST2-8624 in *Escherichia coli* O157:H7. FEMS Immunol Med Microbiol. Apr. 2010;58(3):322-9. (Year: 2010).*
Imlay JA, Linn S. Mutagenesis and stress responses induced in *Escherichia coli* by hydrogen peroxide. J Bacteriol. Jul. 1987;169(7):2967-76. (Year: 1987).*
Comeau et al., "Phage-Antibiotic Synergy (PAS): beta-Lactam and Quinolone Antibiotics Stimulate Virulent Phage Growth", PLoS ONE, 2007, vol. 2, Issue 8, e799, 4 pages.

* cited by examiner

*Primary Examiner* — Nicole Kinsey White
*Assistant Examiner* — Ruixue Wang
(74) *Attorney, Agent, or Firm* — Vorys, Sater, Seymour and Pease LLP; Mih Suhn Koh

(57) ABSTRACT

Provided is a method and composition using ROS to increase the production of bacteriophage. According to the subject matter, a production amount of bacteriophage is increased several times in the presence of the sublethal concentration of ROS for host bacteria. Therefore, the method and composition of the subject matter can be useful for producing bacteriophage, which is used as an alternative to antibiotics that cause a serious resistance problem.

2 Claims, 5 Drawing Sheets

COMPOSITION AND METHOD FOR INCREASING PRODUCTION OF BACTERIOPHAGE USING REACTIVE OXYGEN SPECIES

BACKGROUND OF THE INVENTION

Field of the Invention

The technical field of the present disclosure relates to production of bacteriophage.

Description of the Related Art

The emergence of pathogenic bacteria having resistance to antibiotics is causing global problems and thus there is an urgent need to develop agents that can replace antibiotics.

Bacteriophages are bacterial viruses that specifically infect certain bacteria and kill them through complex lysis processes involving many different proteins. Bacteriophages are highly specific for their host bacteria, so the possibility of using bacteriophages as antibiotics was considered before the development of antibiotics. However, the lack of understanding of bacteriophage and the development of antibiotics have reduced their usefulness as antibiotics.

However, recently with the accumulation of research data on bacteriophages, the development of antibiotics that use bacteriophages to treat and prevent bacterial infection is on the rise as an alternative to solve the problem caused by antibiotic overuse.

U.S. Pat. No. 7,622,293 discloses bacteriophage specific to *Pseudomonas* and its use.

KR Patent No. 941892 discloses bacteriophage specific to *Salmonella gallinarum* and its use.

Also, the production of bacteriophage is known to be increased when used in combination with sublethal concentration of antibiotics (Comeau A M, Tetart F, Trojet S N, Prere M F, Krisch H M. 2007. *Phage-Antibiotic Synergy (PAS): beta-lactam and quinolone antibiotics stimulate virulent phage growth*. PLoS One 2:e799).

However, in order to use bacteriophages in various applications, it is necessary to develop a technology that can increase the production of the bacteriophage and also increase the production without the use of antibiotics.

SUMMARY OF THE INVENTION

The present disclosure is to provide method of dramatically increasing the production of bacteriophages using sublethal concentration of ROS.

In one embodiment of the present disclosure, there is provided a composition for increasing the production of a bacteriophage comprising ROS (Reactive Oxygen Species), wherein the ROS is comprised in the composition at a sublethal concentration for a host bacterium infected by the bacteriophage.

In the present disclosure, various combinations of a host bacterium and a bacteriophage that specifically infects the host bacterium may be employed. For example, the host bacterium is *Escherichia coli* and the bacteriophage that infects *E. coli* is bacteriophage T4; the host bacterium is *Bacillus cereus* and the bacteriophage that infects *Bacillus cereus* is PBBC 03; the host bacterium is *Staphylococcus aureus* and the bacteriophage that infects *Staphylococcus aureus* is phage SA11; the host bacterium is *Enterococcus faecalis* and the bacteriophage that infects *Enterococcus faecalis* is phage PBEF 07 or PBEF 09; the host bacterium is *Escherichia coli* Crooks and the bacteriophage that infects *Escherichia coli* Crooks is phage PBEC 22, PBEC 24, or PBEC 82; or the host bacterium is *Pseudomonas aeruginosa* and the bacteriophage that infects *Pseudomonas aeruginosa* is phage PA22, PA25, or PA26.

Various kinds of ROS which have the effects according to the present disclosure can be used for the present compositions and methods. For example, $H_2O_2$, superoxide, hydroxy radicals, or singlet oxygen may be used.

In other aspect of the present disclosure, there is provided a method of increasing the amount of bacteriophages produced comprising incubating/culturing host bacteria and bacteriophages that specifically infect the host bacteria in the presence of the sublethal concentration of ROS for the host bacteria, whereby the number of bacteriophages produced from the host cell is increased.

For ROS, host bacteria and bacteriophages that specifically infect the bacteria which may be employed for the present methods, mention may be made of those described herein.

In one embodiment, as ROS, $H_2O_2$ is used.

In other embodiment, the incubating/culturing step is performed in liquid or solid media, wherein the sublethal dose of ROS is 0.2 mM for the solid medium, and the sublethal dose of ROS is 4.5 mM for the liquid medium without limitation.

In other aspect, there is provided a use of ROS for increasing the production of bacteriophages in host cells.

For the host bacteria and phages which may be employed for the present use, mention may be made of those described herein.

For the ROS which may be employed for the present use, mention may be made of those described herein.

ADVANTAGEOUS EFFECT

The present methods and composition for increasing the production of bacteriophage using ROS induce the filamentation of host bacteria and delay the lysis of the host bacteria in the presence of the sublethal dose of ROS resulting in producing more numbers of phages leading to the increased production of bacteriophages. In addition, by increasing the plaque size on the solid medium, the detection efficiency of the phage can be greatly improved.

Thus, the present methods and compositions herein can be advantageously used for the production of bacteriophages, particular for use as an alternative to antibiotics causing serious problems of resistance.

DETAILED DESCRIPTION OF THE EMBODIMENTS

Figure 1:
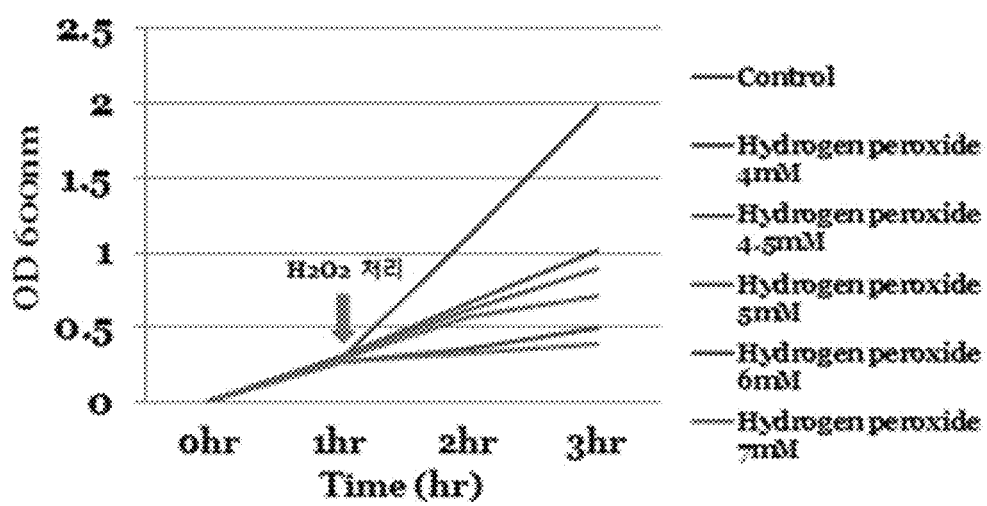
FIG. 1 is a result of the experiments to determine the optimal sublethal concentration of $H_2O_2$ for *E. coli* in liquid culture.

The present disclosure is based on the discovery that the Reactive Oxygen Species (ROS) can increase the number of bacteriophages produced from bacteria in the presence of sublethal concentration of ROS.

In one aspect of the present disclosure, there is provided a composition for increasing the production of a bacteriophage comprising ROS (Reactive Oxygen Species), wherein the ROS is comprised in the composition at a sublethal concentration for a host bacterium infected by the bacteriophage.

In the present disclosure, the term ROS refers to chemically reactive chemical species containing oxygen. Because of the unpaired electrons in reactive oxygen species, the molecules are highly chemically reactive. Examples of ROS include Peroxide, superoxide anion radical ($O_2^-$), singlet oxygen, hydrogen peroxide ($H_2O_2$), hydroxy radical (OH), lipid peroxide, nitric oxide (NO), peroxynitrite ($NO_3^{2-}$), thiol peroxy radicals (R—$SO_2^-$) and the like. In one embodiment, ROS is $H_2O_2$, a superoxide, a hydroxy radical, or a singlet oxygen. Various other ROS that is known to damage DNA/RNA and oxidizes amino acids and fatty acids may also be used in the present disclosure.

In the present disclosure, the term "sublethal concentration" refers to a concentration that affects the growth of the bacteria but is not enough to cause bacterial death. The concentration may vary and be determined depending on the particular ROS, bacteria, and/or culture medium employed. In one embodiment of the present disclosure, the sublethal concentration is defined as a minimum concentration at which the growth rate of bacteria remains constant until 1 hr after the treatment with ROS, which begin to decrease 2 hrs after the treatment with ROS. In one embodiment of the present disclosure, the ROS is hydrogen peroxide and the sublethal concentration is about 0.2 mM in solid media, and about 4.5 mM in liquid media.

Without being intended to be limited by this theory, it was found in the present disclosure that the ROS when present at a sublethal concentration, it induces filamentation of the host bacteria and thus delays the lysis-timing of the host bacteria after being infected by bacteriophages, leading to increasing the number of bacteriophages produced in each bacterium infected.

Bacteria are the host cells for bacteriophages. Usually, one type of bacteriophage only infects one specific type of bacteria. Thus the bacteria employed in the present disclosure can be determined by the bacteriophage the production of which needs to be increased. Both Gram-positive and Gram-negative bacteria may be employed in the present disclosure.

In one embodiment of the present disclosure, Gram-positive bacteria include for example *Staphylococcus aureus* (American Type Culture Collection (ATCC) 13301), *Enterococcus faecalis* (Korean Collection for Type Culture (KCTC) 2011), and *Bacillus cereus* (KCTC 1012) but are not limited thereto, which may be obtained from the institution provided in the parentheses.

In one embodiment of the present disclosure, Gram-negative bacteria include for example *Escherichia coli* Crooks strain (ATCC 8739), *Escherichia coli* K12 MG1655 (ATCC 700926), and *Pseudomonas aeruginosa* (ATCC 13388) but are not limited thereto, which may be obtained from the institution provided in the parentheses.

The bacteriophages the production of which is intended to be increased may be determined by the host cell employed. For example, when the bacteriophage for which the increase in the number of phages produced is intended is phage SA11, *Staphylococcus aureus* may be used as a host bacterium; when the bacteriophage for which the increase in the number of phages produced is intended is phage PBEF 07 or PBEF 09, *Enterococcus faecalis* may be used as a host bacterium; when the bacteriophage for which the increase in the number of phages produced is intended is phage T4, *E. coli* K12 MG1655 may be used as a host bacterium; when the bacteriophage for which the increase in the number of phages produced is intended is phage PBEC 22, PBEC 24, or PBEC 82, *E. coli* Crooks may be used as a host bacterium; when the bacteriophage for which the increase in the number of phages produced is intended is phage PA22, PA25, or PA26, *Pseudomonas aeruginosa* may be used as a host bacterium; when the bacteriophage for which the increase in the number of phages produced is intended is phage PBBC 03, *Bacillus cereus* may be used as a host bacterium. In one embodiment of the present disclosure, *E. coli* K12 MG1655 is used as a host cell to increase the production of bacteriophage T4.

As described above, when reactive oxygen species is present at a sublethal concentration for host bacteria, it induces filamentation of the host cells, which delays the lysis timing of the bacteriophages, resulting in a greater number of phages produced. Thus, various combinations of a host cell and a particular bacteriophage that specifically infects the host cells may be used to increase the bacteriophages produced from the host cells.

The bacteriophage and the information therefor are available from Bacteriophage Bank of Korea (http://www.phagebank.or.kr/).

In the present disclosure, ROS or compositions comprising the same is added to media for bacterial culture. Any media suitable for bacterial culture may be used for the present disclosure as long as the effect of increasing the production of bacteriophages in the presence of sublethal concentration of reactive oxygen species according to the present disclosure is achieved. Either solid or liquid media for bacterial culture may be employed for the present disclosure.

Increased bacteriophage production by the compositions or methods herein may be determined, for example, by comparison with a control group without any reactive oxygen species added.

As described above, more bacteriophages are produced due to a delayed bacterial lysis which is caused by the filamentation of host cells in the presence of sublethal concentration of reactive oxygen species in the culture media.

Thus in other aspect of the present disclosure, there are provided methods of increasing bacteriophage production. In one embodiment, the method comprises a step of incubating a host bacterium and a bacteriophage that specifically infects the host bacterium in the presence of sublethal concentration of ROS for the host bacterium, whereby the number of bacteriophages produced from the host bacterium is increased.

The reactive oxygen species and the concentration which may be employed for the present methods are as described above.

The bacteria and particular bacteriophages for bacterial infection which may be employed in the present method are as described above.

The present disclosure is further explained in more detail with reference to the following examples. These examples, however, should not be interpreted as limiting the scope of the present invention in any manner.

EXAMPLES

Materials and Methods

Phages and *E. coli* strain Bacteriophage T4 and *E. coli* MG1655a as a host cell for T4 were used for the experiments. The bacteria were cultured in LB (Luria-Bertani) medium at 37° C. The phages were all obtained from the Bacteriophage Bank of Korea (http://www.phagebank.or.kr/).

Bacteriophage growth and purification The phages were purified using centrifugation and a glycerol gradient method, as previously described (Kim M S, Kim Y D, Hong S S, Park K, Ko K S, Myung H. 2015. Phage-encoded colanic acid-degrading enzyme permits lytic_phage_infection of a capsule-forming resistant mutant *Escherichia coli* strain. Appl Environ Microbiol 2015 81:900-909). Standard phage techniques were used, as previously described (Sambrook J, Russell D W. 2006. Purification of bacteriophage particles by centrifugation through a glycerol step gradient. CSH Protoc pdb.prot3969).

Statistical analysis. All the data are presented as the mean±standard deviation (SD) of triplicate runs of 3 independent experiments. Statistical significance was determined using Student's t test with P-values<0.05 representing significance.

Bacteria Imaging. The bacterial morphologies were observed under a laser scanning microscope using ZEN software. (Zeiss LSM 700). For sampling, 5~10 ul of the bacteria was dropped on a glass slide and covered with a coverslip. After 20 min of drying in a fume hood, the bacteria were observed using a 100× objective lens. When the bacteria were cultured using a glass-bottom 96-well black plate (Ibidi #89626), the bacteria were fixed with cold acetone and blocked with 1% BSA in PBST for 30 min.

Phage plaque size measurement. Phage plaques were allowed to form on a bacterial lawn and the size measured using a digital caliper.

Example 1

Increase of Bacteriophage Production in the Presence of Sublethal Dose of ROS (Reactive Oxygen Species)

1-1. Determination of Optimal Sublethal Concentration $H_2O_2$ was used as ROS, which was prepared by 1:2 serial dilution. The sublethal concentration was determined as 0.2 mM for the solid medium, and 4.5 mM (FIG. 1) for the liquid medium.

1-2. Analysis of Increasing Phage Production in the Presence of ROS in Liquid Medium.

*E. coli* K12 (MG1655) was cultured overnight. The overnight culture was inoculated at 1:100 (vol:vol) ratio to a 10 ml LB broth in a 50 ml tube and incubated for 1 hr to prepare a fresh culture. When the *E. coli* K12 strain reached an $OD_{600}$ of 0.3, $H_2O_2$ was added at a final concentration of 4.5 mM and incubated further for 1 hr until $OD_{600}$ of 0.5~0.7. Then T4 was added at a multiplicity of infection (MOI) of 0.001 and incubated further for 5 min at 37° C. in a shaking incubator to allow for phage adsorption. Then the culture was centrifuged at 12,000 rmp for 5 min and the supernatant was removed. Ten ml of fresh LB broth was added to the pellet and resuspended. When the resuspension was completed, which was set to 0 min, the resuspend culture was incubated at a 37° Crotary incubator at 0 min, and 500 µl of the culture was taken at 5 minute intervals. Each of the culture was then plated by a double agar overlay and the number of phages were counted.

The same experiments as described above are performed employing various other ROS such as for example, peroxides, superoxides, anionic radicals ($O_2^-$), singlet oxygen, $H_2O_2$, hydroxy radicals (OH), lipid peroxides, Nitric Oxide (NO), Peroxinitrite ($NO_3^{2-}$), Thioperoxiradical ($R-SO_2^-$). It is evident to one of ordinary skill in the art that identical or similar results/effects are obtained using other various ROS without difficulty.

1-3. Analysis of Increasing Phage Production in the Presence of ROS in Solid Medium.

The serially diluted phage solution was plated to a solid medium containing sublethal dose of $H_2O_2$ by using a double agar overlay and the number of phages was counted. *E. coli* cultured in a liquid medium in the presence of sublethal dose of $H_2O_2$ was observed at ×1000 under a light microscopy.

The same experiments as described above are performed employing various other ROS such as for example, peroxides, superoxides, anionic radicals ($O_2^-$), singlet oxygen, $H_2O_2$, hydroxy radicals (OH), lipid peroxides, Nitric Oxide (NO), Peroxinitrite ($NO_3^{2-}$), Thioperoxiradical ($R-SO_2^-$). It is evident to one of ordinary skill in the art that identical or similar results/effects are obtained using other various ROS without difficulty.

Figure 2:
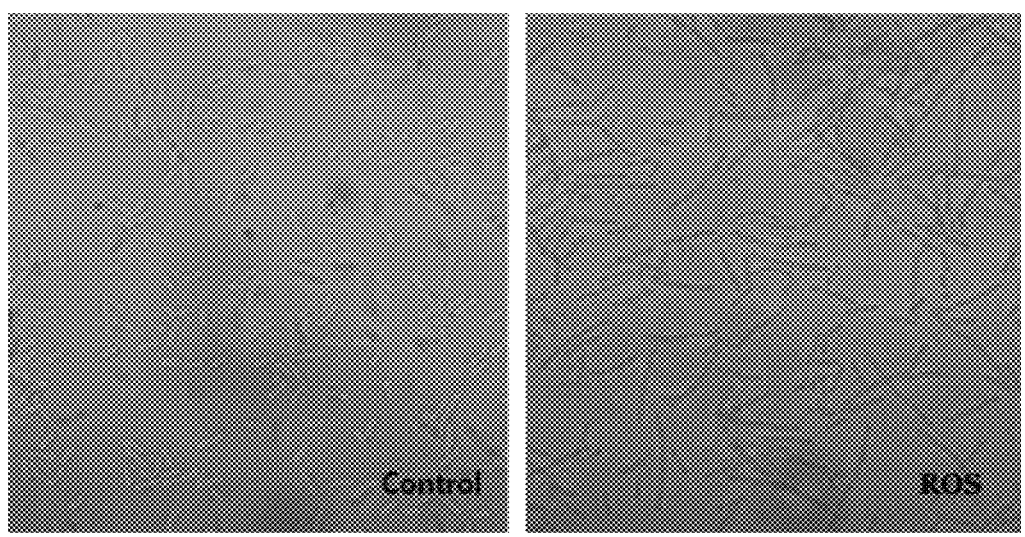
FIG. 2 is a microscopic picture of *E. coli* cultured in the presence of the sublethal concentration of $H_2O_2$ determined in FIG. 1 showing the morphological changes (filamentation) thereof.
Figure 3:
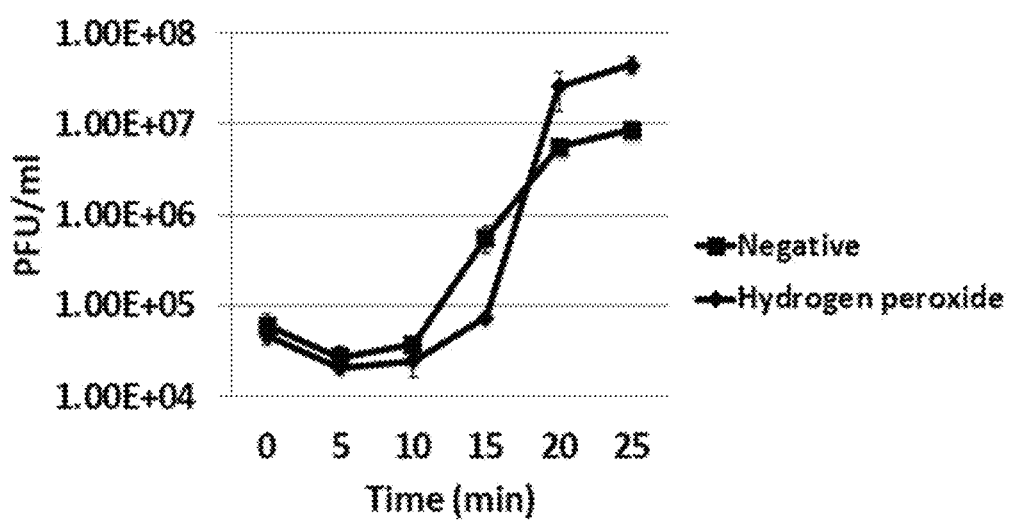
FIG. 3 is one step multiplication curve of bacteriophage T4 in the presence of sublethal concentration of $H_2O_2$ for *E. coli* in liquid culture.

The results are shown in FIGS. 2 to 5. Increase in bacterial length due to bacterial filamentation in the presence of the sub-lethal dose of hydrogen peroxide was observed (FIG. 2). Also, when phages were allowed to infect *E. coli* cultured in the presence of the sub-lethal dose of hydrogen peroxide and one step multiplication was analyzed (FIG. 3), the start of the burst was delayed by 5 min and the size of the burst was increased 6 times compared to the control.

Figure 4:
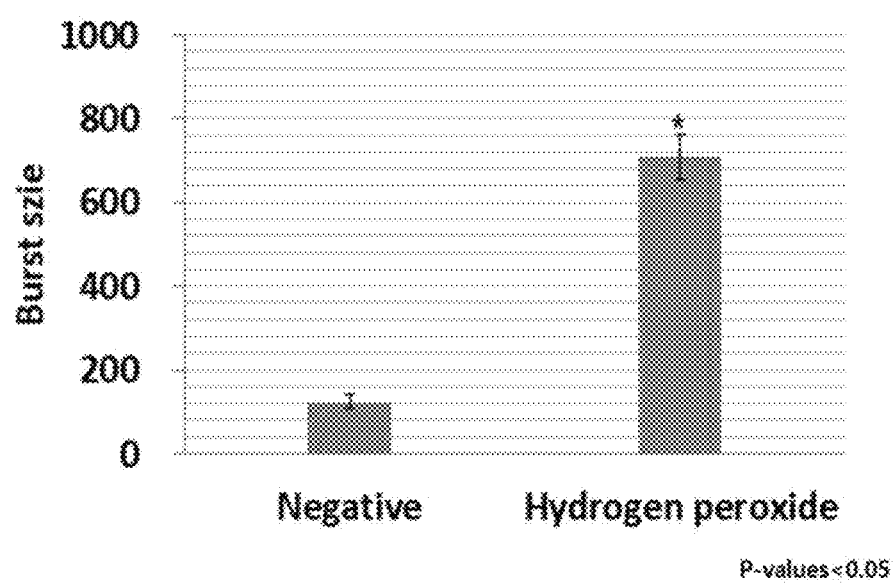
FIG. 4 is a graph showing the burst size of bacteriophage T4 in the presence of sublethal concentration of $H_2O_2$ for *E. coli* in liquid culture.
Figure 5:
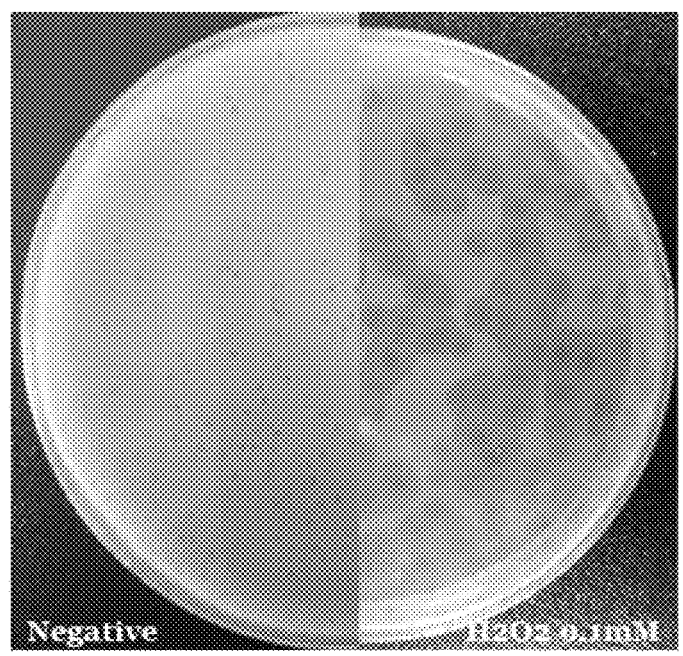
FIG. 5 is a graph showing the size of bacteriophage T4 plaque in the presence of sublethal concentration of $H_2O_2$ for *E. coli* in solid medium.

In addition, the plaque size (diameter), which was analyzed on a solid medium in the presence of the sub-lethal dose of hydrogen peroxide was increased at least 5 times compared to the control (FIGS. 4 and 5).

In conclusion, when the phage production by bacteria in response to ROS stress was analyzed, the bacterial filamentation was clearly observed in the presence of sublethal dose of $H_2O_2$ (FIG. 2) and thus the increase in the phage production was clearly observed in the presence of $H_2O_2$.

The various singular/plural permutations may be expressly set forth herein for sake of clarity. Although a few embodiments of the present disclosure have been shown and described, it would be appreciated by those skilled in the art that changes may be made in this embodiment without departing from the principles and sprit of the invention, the scope of which is defined in the claims and their equivalents.

Unless defined or interpreted otherwise, all technical and scientific terms and any acronyms used herein have the same meanings as commonly understood by one of ordinary skill in the art in the field of the invention. The contents of all publications disclosed as references herein are incorporated herein by reference.

What is claimed is:

1. A composition for increasing the production of a T4 bacteriophage comprising ROS (Reactive Oxygen Species), the T4 bacteriophage, and a host bacterium, wherein the ROS is comprised at the sublethal concentration for the host bacterium infected by the T4 bacteriophage, wherein the ROS is H202, the concentration is 4.5 mM, and the host bacterium is *Escherichia coli*.

2. A method of increasing the production of a lytic bacteriophage comprising incubating a host bacterium and the lytic bacteriophage that specifically infect the host bacterium in the presence of sublethal concentration of ROS for the host bacteria, whereby the production of bacteriophage is increased by increasing burst size of the bacteriophage, wherein the host bacterium is *Escherichia coli* and the bacteriophage that infects *E. coli* is bacteriophage T4; wherein the ROS is H2O2, wherein the incubation is done in a liquid or a solid medium, wherein the sublethal dose of ROS is 0.2 mM for the incubation in the solid medium, and the sublethal dose of ROS is 4.5 mM for the incubation in the liquid medium.

\* \* \* \* \*